United States Patent
Ellis

(12) 
(10) Patent No.: US 6,613,908 B2
(45) Date of Patent: Sep. 2, 2003

(54) METHOD FOR CARBAMOYLATING ALCOHOLS

(75) Inventor: James E. Ellis, Holland, MI (US)

(73) Assignee: Warner-Lambert Company, Morris Plains, NJ (US)

( * ) Notice: Subject to any disclaimer, the term of this patent is extended or adjusted under 35 U.S.C. 154(b) by 0 days.

(21) Appl. No.: 10/056,268

(22) Filed: Jan. 25, 2002

(65) Prior Publication Data

US 2002/0103378 A1 Aug. 1, 2002

Related U.S. Application Data

(60) Provisional application No. 60/265,502, filed on Jan. 1, 2001.

(51) Int. Cl.$^7$ ............................................. C07D 401/14
(52) U.S. Cl. ..................................................... 546/274.4
(58) Field of Search ...................................... 546/274.4

(56) References Cited

U.S. PATENT DOCUMENTS

5,910,506 A  6/1999  Sugimoto

OTHER PUBLICATIONS

Haase, CA 111:59969, 1988.*
B. Loev and M.Kormendy, An Improved Synthesis of Carbamates, J. Org. Chem. 28:3421–3426 (1963).

* cited by examiner

Primary Examiner—D. Margaret Seaman
(74) Attorney, Agent, or Firm—Keith D. Hutchinson; Bryan C. Zielinski; Peter Richardson

(57) ABSTRACT

The present invention includes a method for carbamoylating an alcohol with sodium cyanate in the presence of methanesulfonic acid. The reaction can be conducted under anhydrous conditions. This method is suitable for carbamoylating a molecule including both an alcohol moiety and a basic moiety and/or a molecule including both an alcohol moiety and a sulfenyl moiety, such as the sulfenyl alcohol precursor of the antiviral agent Capravirine.

18 Claims, No Drawings

METHOD FOR CARBAMOYLATING ALCOHOLS

CROSS REFERENCE TO RELATED APPLICATIONS

This application claims benefit of priority from U.S. Provisional Application No. 60/265,502, filed on Jan. 1, 2001.

FIELD OF THE INVENTION

The present invention includes a method for carbamoylating an alcohol with sodium cyanate in the presence of methanesulfonic acid. The reaction can be conducted under anhydrous conditions. This method is suitable for carbamoylating a molecule including both an alcohol moiety and a basic moiety and/or a molecule including both an alcohol moiety and a sulfenyl moiety, such as the sulfenyl alcohol precursor of the antiviral agent Capravirine.

BACKGROUND OF THE INVENTION

The non-nucleoside reverse transcriptase inhibitor known as Capravirine can be synthesized through a route employing chlorosulfonyl isocyanate (CSI) to convert a penultimate Capravirine sulfenyl alcohol to the corresponding carbamate, Capravirine. CSI carbamoylates alcohols in high yield under desirable conditions, but has special shipping and handling requirements due to being highly reactive with water. In addition, CSI is currently available on commercial scale from only two sources, each of which is outside the U.S. These factors along with safety considerations make CSI undesirable as a reagent for the transformation of an alcohol to a carbamate.

A long-used method for carbamoylating alcohols employs sodium cyanate in the presence of trifluoroacetic acid and an inert solvent. The method achieves high yields with a variety of alcohols, but does not work for all alcohols. This synthesis proceeds through generating cyanic acid in situ by the reaction of sodium cyanate with an acid. A widely cited paper on this method by B. Loev and M. Kormendy (J. Org. Chem. 1963, 28, 3421) describes trifluoroacetic acid (TFA), as opposed to other acids, as necessary for obtaining carbamates in good yield. For example, this paper describes that substitution of methanesulfonic acid for trifluoroacetic acid reduces yields of carbamate to only trace levels.

There remains a need for a method for carbamoylating alcohol moieties in molecules also including a basic moiety and/or a sulfenyl moiety, such as Capravirine, and employing an acid other than trifluoroacetic acid.

SUMMARY OF THE INVENTION

The present invention includes a method for carbamoylating an alcohol with sodium cyanate in the presence of methanesulfonic acid. The reaction can be conducted under anhydrous conditions. This method is suitable for carbamoylating a molecule including both an alcohol moiety and a basic moiety, such as the sulfenyl alcohol precursor of the antiviral agent Capravirine. This method is also suitable for carbamoylating a molecule including both an alcohol moiety and a sulfenyl moiety, such as the sulfenyl alcohol precursor of the antiviral agent Capravirine.

In one embodiment, the method includes contacting the alcohol with sodium cyanate in the presence of methanesulfonic acid under anhydrous conditions. In another embodiment, the method carbamoylates an alcohol moiety of a molecule also including a nitrogen heterocycle, a sulfenyl moiety, or both, the method including contacting the molecule with sodium cyanate in the presence of methanesulfonic acid. In an additional embodiment, the method carbamoylates Capravirine sulfenyl alcohol, the method including contacting Capravirine sulfenyl alcohol with sodium cyanate in the presence of methanesulfonic acid. Each of these reactions can be carried out under anhydrous conditions, preferably in an inert solvent, such as acetonitrile. The method can also include quenching the reaction and recovering or purifying a resulting carbamate.

The present invention also includes a method for carbamoylating an alcohol with sodium cyanate, potassium cyanate, cesium cyanate, or a mixture thereof in the presence of acetic acid, sulfuric acid, or a mixture thereof. The reaction can be conducted under anhydrous conditions. This method is suitable for carbamoylating a molecule including both an alcohol moiety and a basic moiety. This method is also suitable for carbamoylating a molecule including both an alcohol moiety and a sulfenyl moiety.

DETAILED DESCRIPTION OF THE INVENTION

Definitions

As used herein, the term "anhydrous" refers to a reaction mixture that is very dry, typically including less than about 1 wt-% water, preferably less than about 0.7 wt-% water, preferably less than about 0.5 wt-% water, or, preferably, devoid of water. According to the present invention, anhydrous conditions suitable for carrying out the present method can be obtained by measures known to those of skill in the art. Preferably the starting alcohol is dried using known procedures for drying alcohols to a water content of less than about 0.2 wt-%. Typically, commercially available reagent grades of the solvent (e.g., acetonitrile) and acid (e.g. methanesulfonic acid) can be used without drying. Typically these commercially available solvents and acids are essentially anhydrous.

As used herein, the term "base" refers to any of a large class of compounds with one of more of properties such as bitter taste, slippery feeling in solution, ability to turn litmus paper blue and to cause other indicators to take on characteristic colors, or ability to react with (neutralize) acids to form salts. Such bases include both Lowry-Bronsted bases and Lewis bases. Lowry-Bronsted base refers to any molecular or ionic substance that can combine with a proton (hydrogen ion) to form a new compound. A Lewis base refers to any substance that provides a pair of electrons for a covalent bond with a Lewis acid. As used herein, a "basic moiety" is a fragment of a basic compound, which fragment would be a base if it were a compound itself. A compound including a basic moiety is a base. Bases and basic moieties include nitrogen heterocycles.

As used herein, "nitrogen heterocycle" refers to any carbon-containing closed-ring structure that includes a nitrogen atom. Examples of nitrogen heterocycles include pyrrole (azole), 2H-pyrrole, 3H-pyrrole, pyrazole (1,2-diazole), imidazole, 2H-imidazole, 1,2,3-triazole, 1,2,4-triazole, isoxazole, oxazole, thiazole, isothiazole, 1,2,3-oxadiazole, 1,2,4-oxadiazole (azoxime), 1,2,5-oxadiazole (furazan), 1,3,4-oxadiazole, 1,2,3,4-oxatriazole, 1,2,3,5-oxatriazole, 3H-1,2,3-dioxazole, 1,2,4-dioxazole, 1,3,2-dioxazole, 1,3,4-dioxazole, 5H-1,2,5-oxathiazole, pyridine, pyridazine, pyrimidine, pyrazine, piperazine, s-triazine (1,3,5-triazine), as-triazine (1,2,4-triazine), v-triazine (1,2,3-triazine), 4H-1,2-oxazine, 2H-1,3-oxazine, 6H-1,3-oxazine, 6H-1,2-oxazine, 1,4-oxazine, 2H-1,2-oxazine, 4H-1,4-oxazine, 1,2,5-oxathiazine, 1,4-oxazine, o-isoxazine, p-isoxazine, 1,2,5- isoxazine, 1,2,5-oxathiazine, 1,2,6-oxathiazine, 1,4,2-oxadiazine, 1,3,5,2-oxadiazine, morpholine (tetrahydro-p-isoxazine), azepine, 1,2,4-aiazepine, indole, 3H-indole (indolenine), 1H-isoindole, cyclopental[b]pyridine, pyrano[3,4-b]-pyrrole, indazole, indoxazine (benzisoxazole), benzoxazole, anthranil, quinoline, isoquinoline, cinnoline, quinazoline, naphthyridine, pyrido[3,4-b]-pyridine, pyrido[3,2-b]-pyridine, pyrido[4,3-b]-pyridine, 2H-1,3-benzoxazine, 2H-1,4-benzoxazine, 1H-2,3-benzoxazine, 4H-3,1-benzoxazine, 2H-1,2-benzoxazine, 4H-1,4-benzoxazine, carbazole, acridine, quinoxaline, purine, and the like.

As used herein, "sulfenyl group", "sulfenyl moiety", or "sulfenyl" refers to a compound including a group having the structure RS-, in which R is an organic moiety but not hydrogen. Sulfenyl groups include sulfides (thioethers). As used herein, "sulfide" or "thioether" refers to a compound including or group having the structure RSR', in which R and R' are each an organic moiety but not hydrogen.

As used herein, the term "Capravirine sulfenyl alcohol" refers to a compound represented by the structural formula:

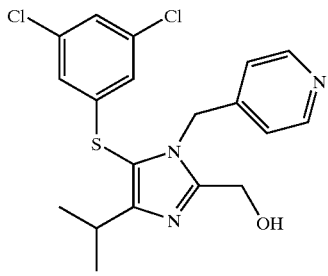

As used herein, the term "Capravirine" refers to a compound represented by the structural formula:

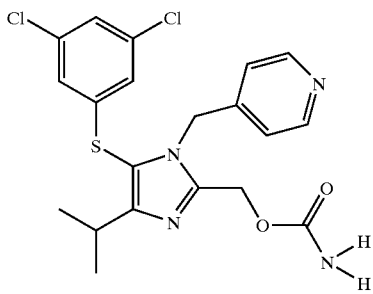

As used herein, the term "about" modifying the quantity of an ingredient, the ratios of ingredients, or temperatures employed in the methods of the invention refers to variation in the numerical quantity that can occur, for example, through typical weighing, measuring, liquid handling, drying, or temperature control procedures used for making reaction mixtures in the real world; through inadvertent error in these procedures; through differences in the manufacture, source, or purity of the ingredients employed to carry out the methods; and the like. Whether or not modified by the term "about", the claims include equivalents to the quantities.

Method of Carbamoylating an Alcohol

The present invention includes a method of carbamoylating an alcohol. In an embodiment the method employs anhydrous conditions and methanesulfonic acid for carbamoylating an alcohol with sodium cyanate. Preferably the alcohol is a moiety of a molecule also including a basic group. Preferably the alcohol is a moiety of a molecule also including either a nitrogen heterocycle, a sulfenyl group, or both. A preferred product of the carbamoylation reaction is a carbamate with a structure otherwise derived from the original alcohol.

In a preferred embodiment, the alcohol is a moiety of the sulfenyl alcohol precursor to the antiviral agent Capravirine. Scheme I, below, illustrates both the precursor and Capravirine.

Scheme I
Carbamoylating the precursor sulfenyl alcohol of Capravirine to Capravirine

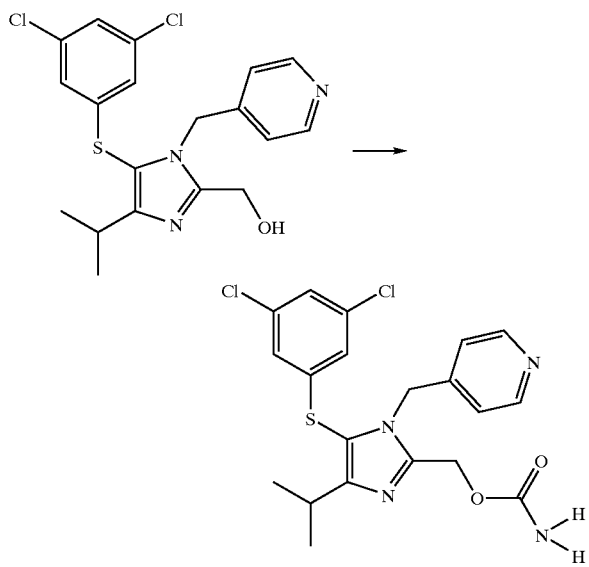

In one embodiment, the method employs sodium cyanate in the presence of methanesulfonic acid for carbamoylating an alcohol moiety in a molecule also including a basic group. Preferably, the reaction is carried out under anhydrous conditions. Preferably the alcohol is a moiety of a molecule also including either a nitrogen heterocycle, a sulfenyl group, or both. In a preferred embodiment, the alcohol is a moiety of the sulfenyl alcohol precursor to the antiviral agent Capravirine.

In another embodiment, the method employs sodium cyanate in the presence of methanesulfonic acid for carbamoylating an alcohol moiety in a molecule also including a sulfide or sulfenyl group. Preferably, the reaction is carried out under anhydrous conditions. Preferably the alcohol is a moiety of a molecule also including a nitrogen heterocycle. In a preferred embodiment, the alcohol is a moiety of the sulfenyl alcohol precursor to the antiviral agent Capravirine.

Reaction Conditions

The method of the present invention can be carried out under a range of conditions, which are described in greater detail below.

Controlling the stoichiometry of the reagents can advantageously increase the yield of the desired carbamate product. Controlling this stoichiometry can also advantageously reduce or minimize the yield of the corresponding allophanate impurity. For example, the molar ratio of methanesulfonic acid to the alcohol can be varied over a broad range. Preferred molar ratios of methanesulfonic acid to the alcohol include about 5 to about 20, more preferably about 9 to about 10. By way of further example, the molar ratio of sodium cyanate to the alcohol can be varied over a range. Preferred molar ratios of sodium cyanate to the alcohol include about 1.5 to about 2.0, preferably about 1.6 to about 1.7, more preferably about 1.65. A preferred reaction mixture includes as molar ratios of reagents: methanesulfonic acid to the alcohol at about 9 to about 10; and sodium cyanate to the alcohol at about 1.65. Reagents at these ratios are particularly advantageous for carbamoylating the sulfenyl alcohol precursor of the antiviral agent Capravirine.

The reaction solvent can be selected to advantageously increase the yield of the desired carbamate product. Preferred solvents are inert, readily made anhydrous, or both. Preferred solvents include ethyl acetate, tetrahydrofuran, and acetonitrile. More preferred solvents include acetonitrile.

The reaction temperature can be selected to advantageously increase the yield of the desired carbamate product. The reaction temperature can also be selected to advantageously reduce or minimize the yield of the corresponding allophanate impurity. The reaction temperature can vary over a wide range. Preferred ranges for the reaction temperature include about −25 to about +40° C., preferably about −10 to about 0° C.

Anhydrous conditions are preferred for carbamoylating alcohols according to the present method. Anhydrous conditions can include the presence of small amounts of water. Preferably, if water is present, the water content is less than about 1 wt-%, preferably less than about 0.7 wt-%, preferably less than about 0.5 wt-%.

According to the present invention, in certain circumstances, the reaction can be run with reagents other than sodium cyanate and methane sulfonic acid. For example, for certain alcohols, carbamoylation can occur with cyanates such as potassium cyanate, cesium cyanate, or a mixture thereof. For certain alcohols, carbamoylation can occur with acids similar to methanesulfonic acid, such as acetic acid, sulfuric acid, or a mixture thereof.

The carbamoylation reaction mixture can be assembled for the reaction and manipulated during the reaction by various methods known to those of skill in the art of running organic reactions. The reaction mixture is ultimately formed by contacting the alcohol with sodium cyanate in the presence of methanesulfonic acid, preferably under anhydrous conditions. Contacting or mixing the reagents provides a reaction mixture suitable for reacting the alcohol and the sodium cyanate. The reaction mixture can be formed by adding reagents in any of several different orders. Preferably, the alcohol, sodium cyanate, and an inert solvent are mixed, followed by adding methanesulfonic acid to this initial mixture. Preferably, cooling the initial mixture reduces its temperature to, for example, about −10° C. before adding the methanesulfonic acid. Adding methanesulfonic acid preferably proceeds slowly, e.g., dropwise, while maintaining a reduced temperature, preferably below about 0° C.

Following addition of methanesulfonic acid, gentle agitation of the reaction mixture at a reduced temperature allows the reaction to proceed to advantageously high yields. Gentle agitation can be accomplished, for example, by stirring. Preferred reduced temperatures for progress of the reaction include about −10 to about 0° C. The reaction can proceed for up to about 8 to about 10 hours, or longer. The duration of the reaction can be monitored or decided by one of skill in the art of running organic reactions.

After the desired time, quenching can stop or slow the carbamoylation reaction. Quenching can be accomplished by any of a variety of methods known to those of skill in the art such as cooling, reducing the concentration of one or more reagents, consuming one or more reagents, or the like. Preferably, quenching includes adding water to the reaction mixture. With or without quenching, any carbamate produced in the reaction can be recovered and/or purified from the reaction mixture by methods known to those of skill in the art of running organic reactions.

The present invention may be better understood with reference to the following examples. These examples are intended to be representative of specific embodiments of the invention, and are not intended as limiting the scope of the invention.

EXAMPLES

Example 1

The Method of Loev and Kormendy

Loev and Kormendy (supra) employed trifluoroacetic acid and sodium cyanate for carbamoylating an alcohol. These reagents were used for initial studies of carbamoylating an alcohol including a sulfenyl group and a basic moiety.

Materials and Methods

Capravirine Sulfenyl Alcohol

In this study the alcohol was the sulfenyl alcohol precursor to the antiviral agent Capravirine. Capravirine sulfenyl alcohol was prepared by the following procedure:

Benzyloxy (4-isopropyl-1-(4-pyridyl)methyl)-1H-imidazol-2-yl) methane dioxalate (171.6 g, 0.342 moles) was slurried into toluene (460 mL) and water (150) mL. The mixture was stirred and cooled to less than 10° C. Charged the 32% aqueous solution of KOH to the mixture slowly with cooling to a final pH of 11–12. The organic layer was separated and washed with water and then with saturated sodium chloride solution. The toluene solution of benzyloxy ((4-isopropyl-1-1-(4-pyridyl)methyl)-1H-imidazol-2-yl) methane was dried by azeotropic distillation of the toluene.

Bis (3,5-dichlorophenyl) disulfide (71.6 grams, 0.201 moles) was dissolved in toluene (180 mL) and cooled to less than 10° C. in an inerted pressure flask. The pressure flask was placed under a vacuum blank and chlorine (30.8 grams, 0.434 moles) was charged at 0–10° C. The reaction was then stirred at 0–10° C. for one half hour. The excess chlorine was removed from the 3,5-dichlorophenyl sulfenyl chloride solution using alternating vacuum and nitrogen purges.

N-methylmorpholine (41.6 gram, 0.411 moles) was charged to the toluene solution of benzyloxy ((4-isopropyl-1-(4-pyridyl)methyl)-1H-imidazol-2-yl) methane from above. The resulting solution was slowly added to the 3,5-dichlorophenyl sulfenyl chloride solution while maintaining temperature at 0–10° C. Once addition has been completed, the sulfenyl ether reaction mixture was stirred at 0–10° C. for about 12 hours. The reaction mixture was then washed with water at a pH of 4 to 7. Concentrated hydrochloric acid (700 mL) was added to the sulfenyl ether layer and heated at 70 to 80° C. for about 7 hours. The reaction was cooled and the aqueous product layer separated. Methanol (92 mL) was added to the aqueous solution. The solution was adjusted to a pH of 2 with dilute sodium hydroxide solution with cooling. Ethyl acetate (460 mL) was added and the aqueous layer was adjusted to a pH of 9. The ethyl acetate layer was separated and water (215 mL) and additional ethyl acetate was added to it. The mixture was adjusted to a pH of 1.5 using concentrated hydrochloric acid with cooling. The aqueous product layer was separated. Methanol (428 ml) was added to the aqueous solution. The solution was adjusted to a pH of 4 with 30% sodium hydroxide solution. The resulting slurry was adjusted to a final pH of 6 using a sodium bicarbonate solution. The slurry was stirred at 30 to 40° C. for about one hour and then cooled to 0–10° C. for about five hours. The slurry was filtered and washed with cold aqueous methanol. The product was dried to provide Capravirine sulfenyl alcohol (121 g, 86.7% yield) with a purity of 99.7% by area normalization upon HPLC.

Preparation of Capravirine

Briefly, the carbamoylation was carried out employing trifluoroacetic acid (TFA) and acetonitrile as solvent. Capravirine sulfenyl alcohol (20.4 g, 0.05 mole), sodium cyanate (5.35 g, 0.0825 mole) and acetonitrile were charged to a 500 ml 3 neck round bottom flask. The slurry was cooled to −10° C., then TFA (11.5 mL) was added dropwise while keeping the temperature below 0° C. The reaction mixture was stirred at −5±5° C. for about 8–10 hours until the reaction was complete. The yield of Capravirine was then determined.

Results

For the sulfenyl alcohol precursor to Capravirine, trifluoroacetic acid gave very poor conversion to the desired carbamate; the in process conversion was 3.3%.

Example 2

Carbamoylating an Alcohol with Sodium Cyanate in the Presence of Sulfuric or Acetic Acid The carbamoylation of an alcohol including a sulfenyl group and a basic moiety with sodium cyanate was investigated in the presence sulfuric acid or acetic acid.

Materials and Methods

Capravirine sulfenyl alcohol was obtained as described above in Example 1. Also as in Example 1, other reagents were the finest commercial grades and were used without further purification.

The conversion of Capravirine sulfenyl alcohol to Capravirine was accomplished as described in Example 1, with the following changes. Sulfuric acid or acetic acid were employed in place of trifluoroacetic acid. Thus, the slurry was cooled to −10° C., then sulfuric acid (18 mL), or acetic acid (30 mL) was added dropwise while keeping the temperature below 0° C.

Results

Sulfuric acid and acetic acid provided higher yields than trifluoroacetic acid. The in process conversions of carbamoylated alcohol were 17.5% with sulfuric acid and 7.8% with acetic acid. Sulfuric acid contains about 4% water by weight.

Example 3

Carbamoylating an Alcohol with Sodium Cyanate in the Presence of Methanesulfonic Acid The carbamoylation of alcohols with sodium cyanate was investigated under various reaction conditions in the presence of acid to yield a suitable method.

Materials and Methods

Materials

Capravirine sulfenyl alcohol was obtained as described above in Example 1. Also as in Example 1, other reagents were the finest commercial grades and were used without further purification.

Preparation of Capravirine

The carbamoylation of Capravirine sulfenyl alcohol to Capravirine was studied under a variety of conditions to determine a suitable method of conducting this reaction. Each of the various conditions was tested by a protocol similar to that reported in the paragraph below for a very effective set of conditions.

Capravirine sulfenyl alcohol (20.4 g, 0.05 mole), sodium cyanate (5.35 g, 0.0825 mole) and acetonitrile were charged to a 500 ml 3 neck round bottom flask. The slurry was cooled to −10° C., then methanesulfonic acid (50 ml, 0.75 mole) was added dropwise while keeping the temperature below 0° C. The reaction mixture was stirred at −5±5° C. for about 8–10 hours until the reaction was complete.

The reaction was quenched by adding 100 mL water and acetonitrile was removed by vacuum distillation. The aqueous solution of the product was then neutralized to pH 6–7 with approximately 60 g 50% sodium hydroxide solution. The product was extracted with 100 mL of ethyl acetate. The ethyl acetate layer was separated and charged with 10 mL acetic anhydride. The mixture was heated to reflux for 2 hours then cooled to room temperature. The reaction mixture was quenched with water and the acetic acid neutralized using sodium carbonate.

The ethyl acetate layer was separated and concentrated to about 70 mL. 50 mL of heptane was added to crystallize the product. After cooling to 5° C. for 3 hours, the product slurry was filtered and dried to give about 18 g of Capravirine which assayed 99% by area normalization with 0.45% allophanate. $^1$H NMR (200 MHZ, $CDCl_3$) 1.3 (6H, d), 3.2(1H, m), 5.2(2H, s), 5.3(1H, s), 6.7(2H, d), 6.8 (2H, m), 7.0(1H, m), 8.4(2H, m).

Results

The reaction of an alcohol with sodium cyanate to produce the corresponding carbamate was found to proceed under a variety of conditions.

Controlling the stoichiometry of the reagents advantageously increased the yield of the desired carbamate product. The molar ratio of methanesulfonic acid to the alcohol was varied over a broad range. Effective conversion (yields of more than about 85%) was observed at molar ratios of methanesulfonic acid to the alcohol of 5 to 20, with the greatest observed conversion (95% yield) at a ratio of 9 to 10. The molar ratio of sodium cyanate to the alcohol was varied over a range. Effective conversion (yields of more than about 85%) was observed at molar ratios of sodium cyanate to the alcohol of 1.5 to 2.0, with the greatest observed conversion (95% yield) at a ratio of 1.65.

The reaction solvent was varied to increase the yield of the desired carbamate product. Effective conversion (yields of more than about 80%) was obtained with several inert solvents, ethyl acetate, tetrahydrofuran, and acetonitrile. The greatest conversion (95% yield) was achieved with acetonitrile as solvent.

The reaction temperature was varied to increase the yield of the desired carbamate product. The reaction temperature was varied over a wide range. Effective conversion (yields of more than about 80%) was observed at temperatures between −25 and +40° C., with the greatest observed conversion (95% yield) at a temperature of about −10 to about 0° C.

The amount of water in the reaction mixture varied to increase the yield of the desired carbamate product. The amount of water was varied between effectively anhydrous conditions (obtained as described above) and up to about 1% water. Effective conversion (yields of more than about 75%) was observed at up to 1% water, with the greatest observed conversion (95% yield) using an anhydrous reaction mixture.

The amount of allophanate impurity was kept as low as possible to increase the yield of the desired carbamate product. The allophanate impurity was kept low by selecting the stoichiometry of the reagents, the temperature of the reaction, the duration of the reaction, and/or the amount of conversion to Capravirine. In addition, the amount of allophanate impurity was kept as low as possible by monitoring its level during the reaction, and, if its level began to rise, quenching the reaction. Typically, the amount of allophanate impurity is kept below about 0.9% to about 1.2%, preferably below about 0.7%, preferably below about 0.5%.

The yields described for these reactions are process yields. Typically, upon isolation of the Capravirine product, yield is reduced by about 10%, or by as much as 20% in unfavorable cases.

Discussion

Methanesulfonic acid provided excellent conversions of alcohol to the desired carbamate under the conditions described herein. This was surprising, since Loev and Kormendy claimed that methanesulfonic acid gave only traces of carbamates under their reaction conditions.

In addition, carefully controlling the reaction stoichiometry reduces the formation of allophanates, a well known by-product of the reaction of alcohols with cyanic acid. When cyanic acid is used to form carbamates commonly a second molecule of cyanic acid will react with the carbamate product to give an allophanate.

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. A method for preparing Capravirine which has the formula

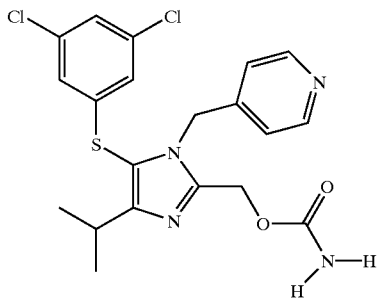

comprising:
carbamoylating Capravirine sulfenyl alcohol which has the formula

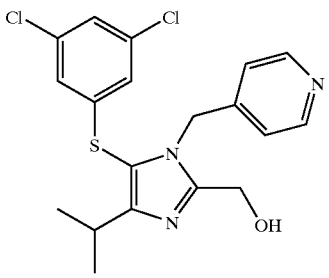

by contacting it with sodium cyanate in the presence of methanesulfonic acid under anhydrous conditions.

2. The method of claim 1, wherein contacting comprises employing a molar ratio of methanesulfonic acid to Capravirine sulfenyl alcohol of about 5 to about 20.

3. The method of claim 1, wherein the molar ratio is about 9 to about 10.

4. The method of claim 1, wherein contacting comprises employing a molar ratio of sodium cyanate to Capravirine sulfenyl alcohol of about 1.5 to about 2.0.

5. The method of claim 1, wherein the molar ratio is about 1.6 to about 1.7.

6. The method of claim 1, wherein the molar ratio is about 1.65.

7. The method of claim 1, wherein contacting comprises employing a molar ratio of methanesulfonic acid to Capravirine sulfenyl alcohol of about 9 to about 10 and a molar ratio of sodium cyanate to Capravirine sulfenyl alcohol at about 1.65.

8. The method of claim 1, wherein contacting comprises employing an inert solvent.

9. The method of claim 1, wherein the solvent comprises ethyl acetate, tetrahydrofuran, acetonitrile, or a combination thereof.

10. The method of claim 1, wherein the solvent comprises acetonitrile.

11. The method of claim 1, comprising contacting at a temperature of about −25° C. to about +40° C.

12. The method of claim 1, comprising contacting at a temperature of about −10° C. to about 0° C.

13. The method of claim 1, wherein anhydrous conditions comprise the presence in the solvent of less than about 1 wt-% water.

14. The method of claim 1, wherein contacting comprises:
mixing Capravirine sulfenyl alcohol, sodium cyanate, and acetonitrile;
cooling the mixture to about −10° C.;
adding methanesulfonic acid to the cooled mixture dropwise while keeping the temperature below 0° C.; and
stirring the mixture including methane sulfonic acid at about −10° C. to about 0° C. for about 8 to 10 hours.

15. The method of claim 1, further comprising quenching the reaction.

16. The method of claim 1, wherein quenching comprises adding water.

17. The method of claim 1, further comprising recovering Capravirine.

18. The method of claim 1, further comprising purifying Capravirine.

* * * * *